United States Patent
Oultram et al.

(12) 
(10) Patent No.: US 6,423,495 B1
(45) Date of Patent: Jul. 23, 2002

(54) AMPLIFICATION OF NUCLEIC ACIDS

(75) Inventors: John Douglas Oultram, Manchester; Jacqueline Clare Coutts, Winsford, both of (GB)

(73) Assignee: Tepnel Medical Limited, Winsford (GB)

( * ) Notice: Subject to any disclaimer, the term of this patent is extended or adjusted under 35 U.S.C. 154(b) by 0 days.

(21) Appl. No.: 09/485,506

(22) PCT Filed: Aug. 12, 1998

(86) PCT No.: PCT/GB98/02427

§ 371 (c)(1), (2), (4) Date: May 15, 2000

(87) PCT Pub. No.: WO99/09211

PCT Pub. Date: Feb. 25, 1999

(30) Foreign Application Priority Data

Aug. 13, 1997 (GB) ................................ 9717061

(51) Int. Cl.$^7$ .................................. C12Q 1/68
(52) U.S. Cl. .................. 435/6; 435/91.1; 435/91.2; 536/25.4
(58) Field of Search .................... 435/6, 91.1, 91.2; 536/25.4

(56) References Cited

U.S. PATENT DOCUMENTS 5,849,479 A * 12/1998 Janjic et al. .................... 435/6
5,858,660 A * 1/1999 Eaton et al. .................... 435/6

* cited by examiner

Primary Examiner—W. Gary Jones
Assistant Examiner—Janell E. Taylor
(74) Attorney, Agent, or Firm—Woodard, Emhardt, Naughton Moriarty & McNett

(57) ABSTRACT

The present invention relates to a method of amplifying a nucleic acid sequence present in a first strand of a double stranded nucleic acid molecule wherein said molecule incorporates an unmodified recognition site for a restriction enzyme capable of cutting the first strand at the 5' end of the sequence therein to be amplified and leaving the 3'-cut region of the second strand projecting beyond the cut site in the first strand. The method further comprises treating said molecule with said enzyme in the presence of a strand displacing polymerase and unmodified nucleotides for incorporation in an extending nucleic acid strand such that there is or becomes hybridised to said 3'-end region of the second strand a primer sequence complementary thereto whereby said primer sequence is extended in the 5' to 3' direction using the second strand as a template to regenerate the restriction endonuclease cut site and displace the sequence to be amplified.

8 Claims, 13 Drawing Sheets

Figure 1:
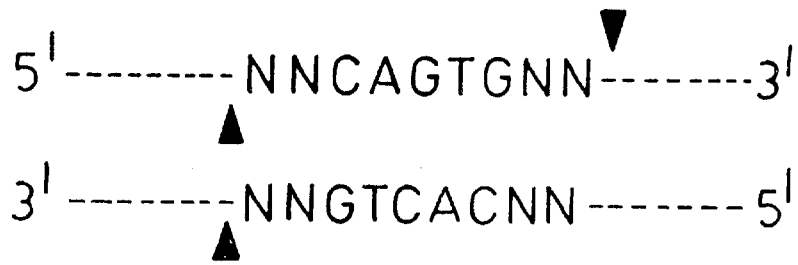

(inverse image). Lane 1, 250 base pair ladder; 2, gap; 3, Isofragment2 (50 fmol); 4, ISOS-0 cycle; 5, ISOS -1 cycle; 6, ISOS -2 cycle; 7, ISOS -3 cycle; 8, ISOS -4 cycle; 9, ISOS -5 cycle; 10, ISOS -6 cycle; 11, ISOS -7 cycle; 12, ISOS -8 cycle; 13, ISOS -9 cycle.

Lanes 1 and 6; Standards (100bp ladder). Lane2; Zero time. Lane3; 20 minutes. Lane 4; 40 minutes. Lane 5; 80 minutes.

(inverse image). Lanes 1 and 15, 250 base pair ladder; 2, gap; 3, Isofragment2 (50 fmol); 4, ISOS-0 cycle; 5, ISOS -1 cycle; 6, ISOS -2 cycle; 7, ISOS -3 cycle; 8, ISOS -4 cycle; 9, ISOS -5 cycle; 10, ISOS -6 cycle; 11, ISOS -7 cycle; 12, ISOS -8 cycle; 13, ISOS -9 cycle; 14, ISOS -10 cycle*.

*The 10 cycle sample was the remainder of the reaction mix and was less than the 20μL taken for other samples Lane 1: 20 bp DNA standard ladder
Lane 2: 760 zmol template input
Lane 3: 76 zmol template input
Lane 4: 7.6 zmol template input
Lane 5: 0.76 zmol template input
Lane 6: Iso-S no template

AMPLIFICATION OF NUCLEIC ACIDS

The present invention relates to the amplification of nucleic acids, i.e. procedures for producing copies of nucleic acid sequences.

As used herein the term "nucleic acid" includes protein nucleic acid (PNA) (i.e. nucleic acids in which the bases are linked by a polypeptide backbone) as well as nucleic acids (e.g. DNA and RNA) having a sugar phosphate backbone.

Various nucleic acid amplification techniques are already known, e.g. the Polymerase Chain Reaction (PCR). However many of these techniques (including PCR) suffer from the disadvantage that various cycles of heating and cooling are required for each amplification reaction. Thus, in a typical amplification reaction, the sequence (in single stranded form) to be amplified is treated with an oligonucleotide capable of hybridising to the sequence at a particular location thereof, the treatment being effected at a temperature (and under other conditions, e.g. buffers etc.) at which the hybridisation will occur. In the next step (which may or may not be effected at the same temperature) a polymerase enzyme is used to extend the oligonucleotide primer (using the original sequence as a template) to produce a strand which is complementary to the original strand and which is hybridised thereto. Subsequently the reaction mixture must be heated to denature the complementary strands and then cooled so that the above described procedure (i.e. primer hybridisation, extension, denaturing) may be repeated.

An alternative amplification procedure known as Strand Displacement Amplification has previously been proposed. This procedure may be effected isothermally but does require the construction of a double stranded nucleic acid molecule incorporating hemi-modified restriction site, more particularly a site modified (in one strand) by the incorporation of a thiolyated adenine. The SDA reaction must be conducted in the presence of a chemically modified base to ensure regeneration of the hemi-modified restriction site. This modified base does however become incorporated in the copy strands produced in the reaction and this is a restriction imposed on the procedure.

According to the present invention there is provided a method of amplifying a nucleic acid sequence present in a first strand of a double stranded nucleic acid molecule comprised of complementary first and second strands wherein said molecule incorporates an unmodified recognition site for a restriction enzyme capable of cutting the first strand at the 5' end of the sequence therein to be amplified and leaving the 3'-end region of the second strand projecting beyond the cut site in the first strand, and said method comprises treating said nucleic acid molecule with said enzyme in the presence of a strand displacing polymerase and unmodified nucleotides for incorporation in an extending nucleic acid strand under conditions such that there is or becomes hybridised to said 3'-end region of the second strand a primer sequence complementary thereto whereby said primer sequence is extended direction using the second strand as a template to re-generate the restriction endonuclease cut site and displace the sequence to be amplified.

By unmodified recognition site we mean that the site consists of unmodified A, G, T and/or C bases.

It will be appreciated that the steps of cutting and extension may be repeated as often as necessary to generate the desired amplification.

An important feature of the invention is that the restriction enzyme is capable of providing a 3'-end region of the second strand which projects beyond the cut site in the first strand. The nucleic acid molecule and/or the nature of the restriction enzyme may be such that only the first strand is cut (i.e. nicked). Alternatively both strands may be cut. In either case, the cut in the first strand einerates a fragment (a 3'-upstream fragment) on the 3' side of the cut in that strand. This fragment may, in certain cases, act as said primer sequence (provided that it remains hybridised to the 3'-end region of the second strand) Alternatively, depending on the length of the fragment and/or the reaction conditions, the fragment may be cleaved from the end region of the second strand to generate a 3'-overhang. It is therefore usually preferred that an oligonucleotide primer (also referred to herein as the FP primer) capable of hybridising to the 3'-end region is additionally incorporated in the reaction to improve the probability of there being a primer sequence hybridised to the 3'-end region of the second strand for effecting the extension/displacement reaction. It will be appreciated that FP primer incorporates all or part of the overhanging sequence produced by the enzyme digestion outlined above.

The manner in which amplification proceeds to effect amplification is described in more detail below but, in brief, the primer sequence is extended in the 5' to 3' direction to displace the sequence to be amplified whilst creating a further copy of that sequence (hybridised to the template strand) and regenerating the restriction site. The processes of cutting the double stranded molecule and extension/displacement are repeated to provide for increasing quantities (i.e. amplification) of the sequence to be amplified.

It is preferred that the nucleic acid molecule incorporates two restriction sites of the type described, one each side of the sequence to be amplified. These restriction sites are ideally the same as each other (so that only one restriction enzyme is required) but may be different. The provision of two restriction sites as described allows for extension/displacement reactions to proceed in opposite directions from either end of the molecule. By providing an excess of FP primers in the reactant mix, these primers may hybridize to the 3'-overhangs, produced by the digestion with the restriction enzyme, allowing production of double stranded molecules incorporating a single restriction site. These double stranded molecules participate in further amplification reactions as described more fully below. As described below, such further reactions produce nucleic acid strands which are not able to bind to the FP primers. In an advantageous development of the invention, the reactant mix includes at least one further type of primer (referred to herein as ISOS primers) incorporating the FP sequence and being capable of hybridising to the nucleic acid strands which are themselves not able to bind to the FP primers per se. The ISOS primers result in generation of further double stranded molecules incorporating a restriction site, such molecules being able to participate in amplification reactions. This channelling of otherwise non-hybridisable single strands back into the amplification process leads to an exponential accumulation of product. Where both ISO-S and FP primers are used, the former will generally be employed at a much lower concentration than the latter, generally at least 10 fold less ISO-S primer than FP primer. The ISO-S primers generally are used at a concentration of between 1 fmol/$\mu$l to 50 pmol/$\mu$l and the FP primers are generally used at a concentration of between 10 fmol/$\mu$l to 500 pmol/$\mu$l. It should be noted that, under conditions in which the cleavage products of restriction enzyme digestion do not become separated prior to the action of the DNA polymerase, the exponential amplification reaction may be performed by the ISOS primers in the absence of FP primers.

The method of the invention may be a solution phase reaction, and must occur under such conditions (of salt concentration, pH, nucleotide concentration etc.) that both the restriction digestion and polymerase extension reactions can occur, though not necessarily simultaneously. Preferred conditions for the method of the invention to be carried out are in a New England Thermopolymerase buffer at pH 8.8, in the presence of 10–20 mM magnesiwn ions, and a nucleotide final concentration of 0.1–1.0 mM.

Theoretically, the target nucleic acid for the amplification may be present in very small amounts, and hence the amplification will find utility in such areas as clinical diagnostics, to detect either the presence or absence of a sequence or, at a more discriminatory level the occurrence of variations of an underlying sequence. Both DNA and RNA might be used as the target for amplification, the later requiring initial reverse transcription to a DNA intermediate.

The restriction enzyme may for example be TspRI but any other enzyme producing the required 3'-end region in the second strand may be used.

The strand displacing polymerase may for example be 9° N polymerase (ex-New England Biolabs), Klenow (exo-) polymerase. Bst polymerase, Vent (exo-) polymerase. or Deep Vent (exo-) polymerase.

The temperature(s) at which the reaction is effected is/are dependent upon the combination of restriction endonuclease and displacing polymerase used in the reaction. Under certain conditions, the restriction endonuclease will effect cutting at the temperature at which the displacing polymerase will effect a copying reaction. Under such conditions, the reaction of the invention may be effected isothermally. It is however also within the scope of the invention that different temperatures are required for cutting and copying so that a two-step thermal cycling reaction may be envisaged. Thermal cycling in this case is not that cycling which is required to perform PCR. In PCR, a strand separation step is an absolute requirement of each cycle of the technique and is usually performed by heating the sample to 95–98° C. No such cyclic strand separation is required in the method of the invention where cycling is used to allow primer annealing or to move between the temperature optima of the enzymes used.

Figure 2:
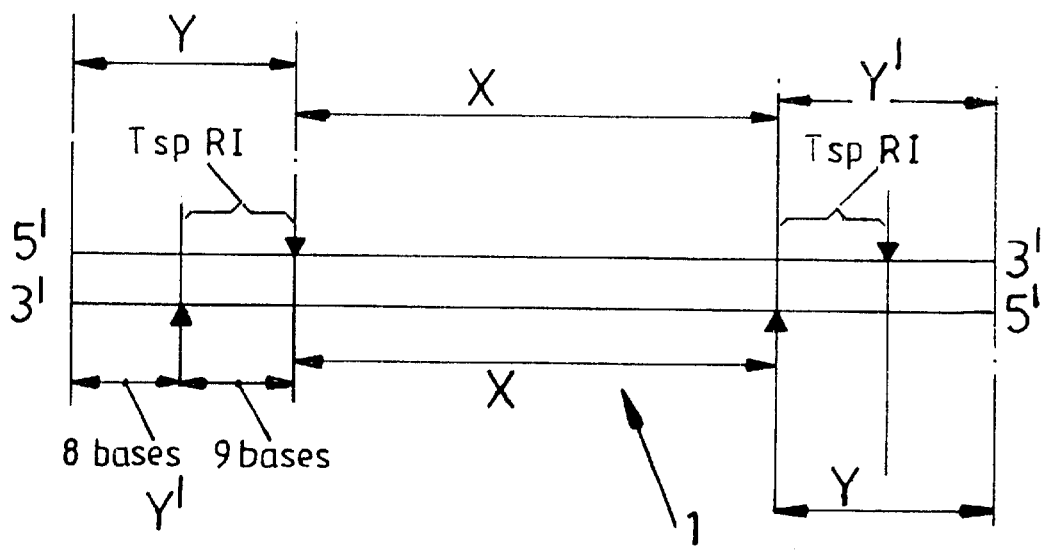
Figure 3A:
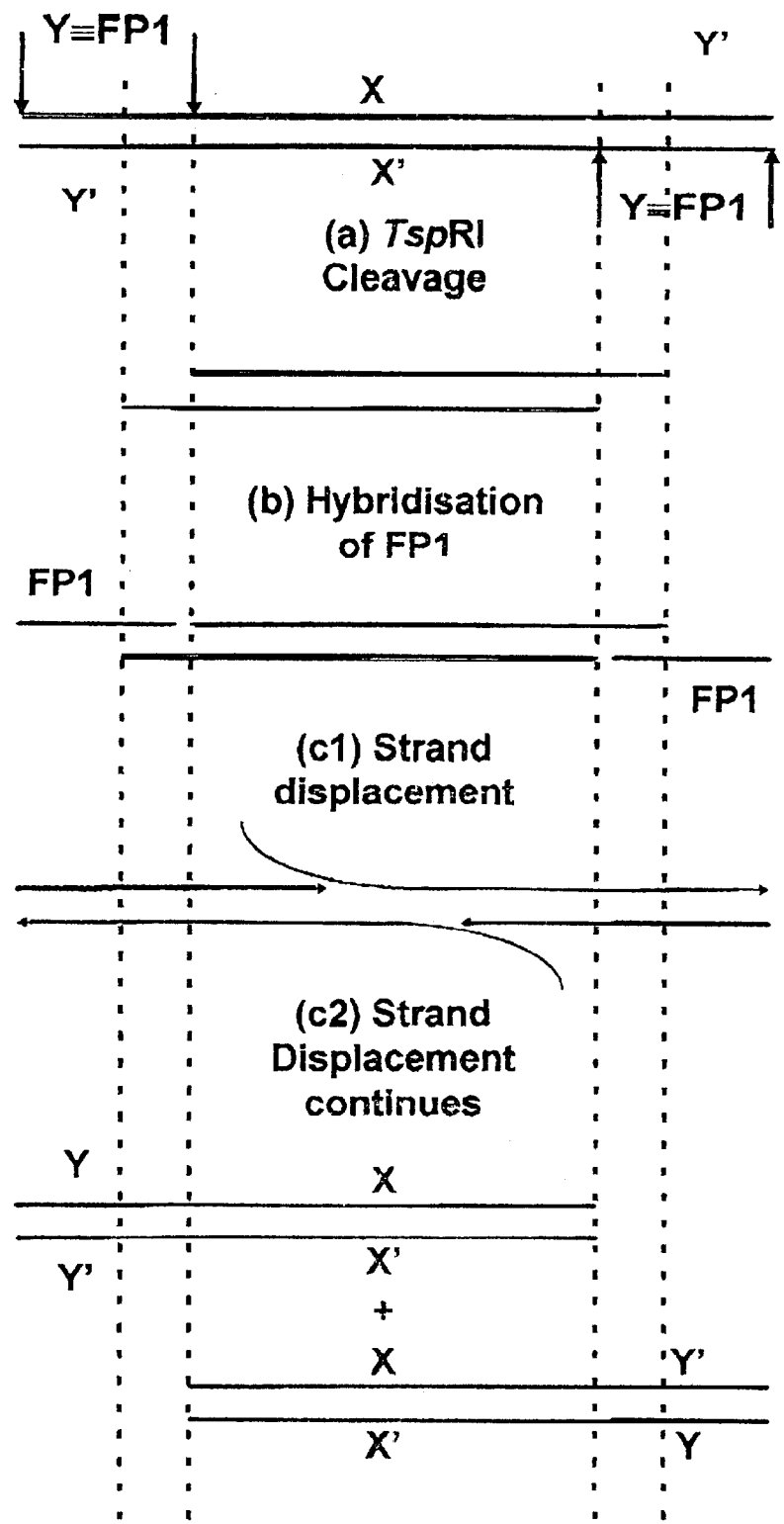
Figure 3B:
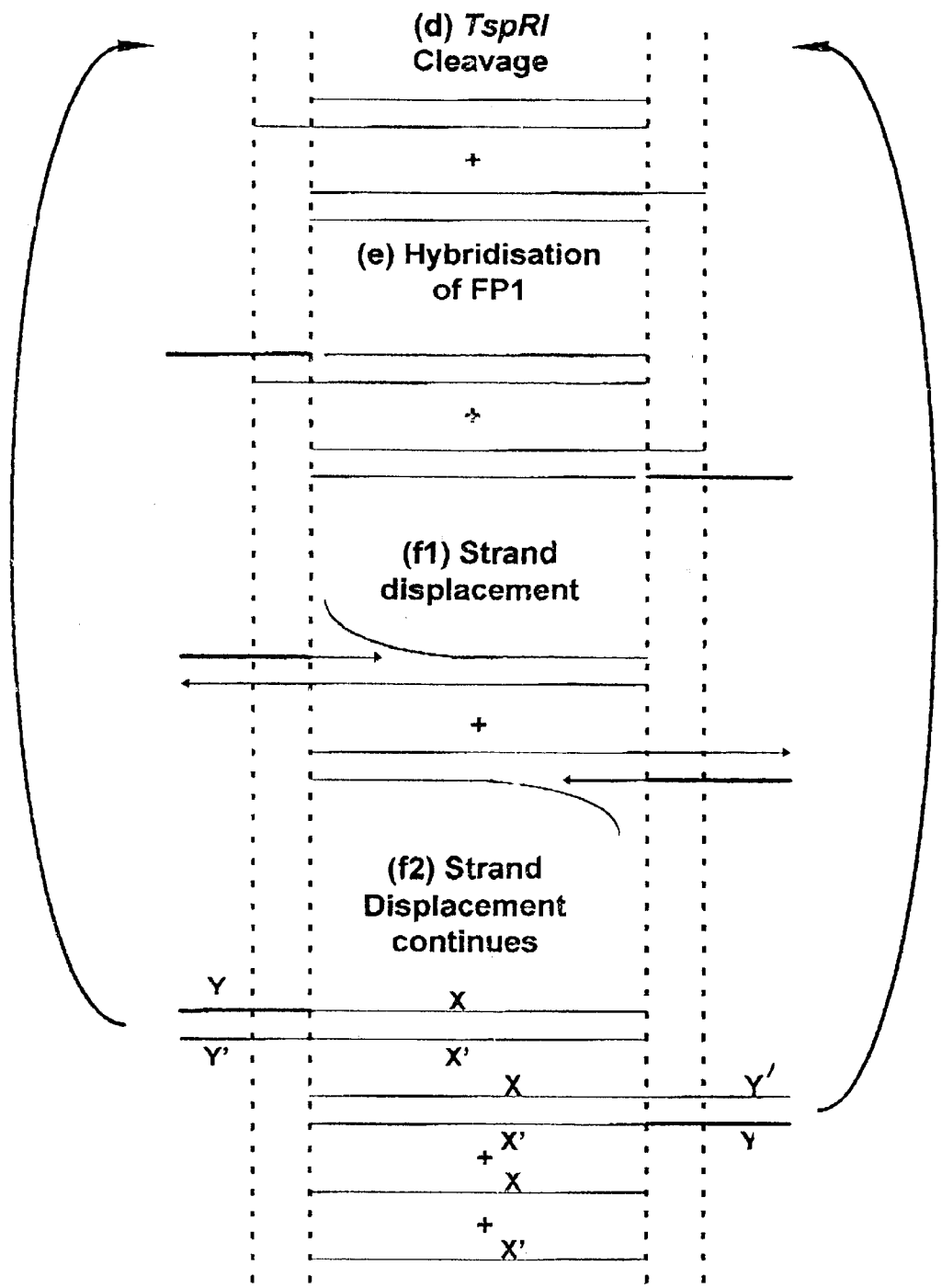
Figure 3C:
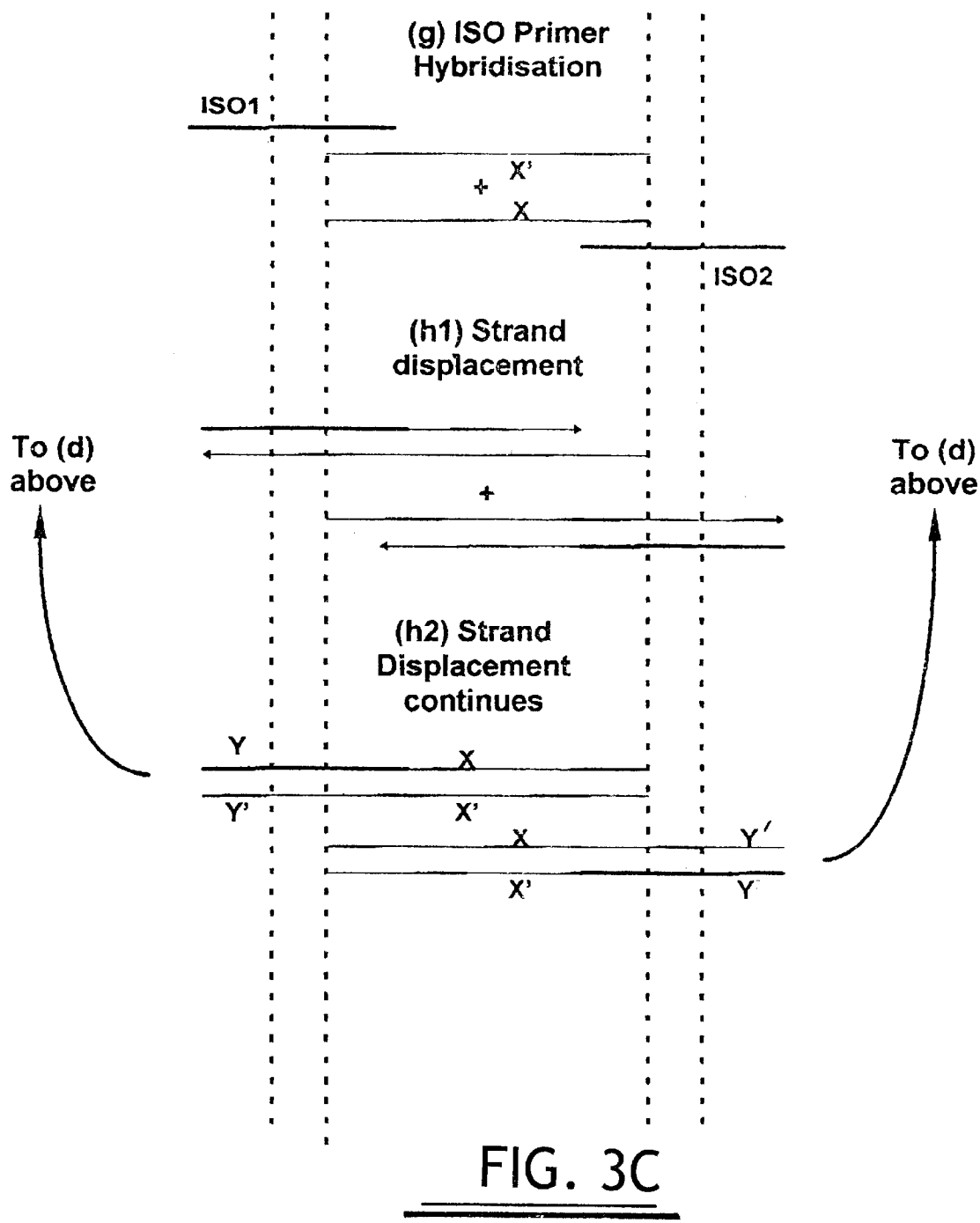
Figure 4A:
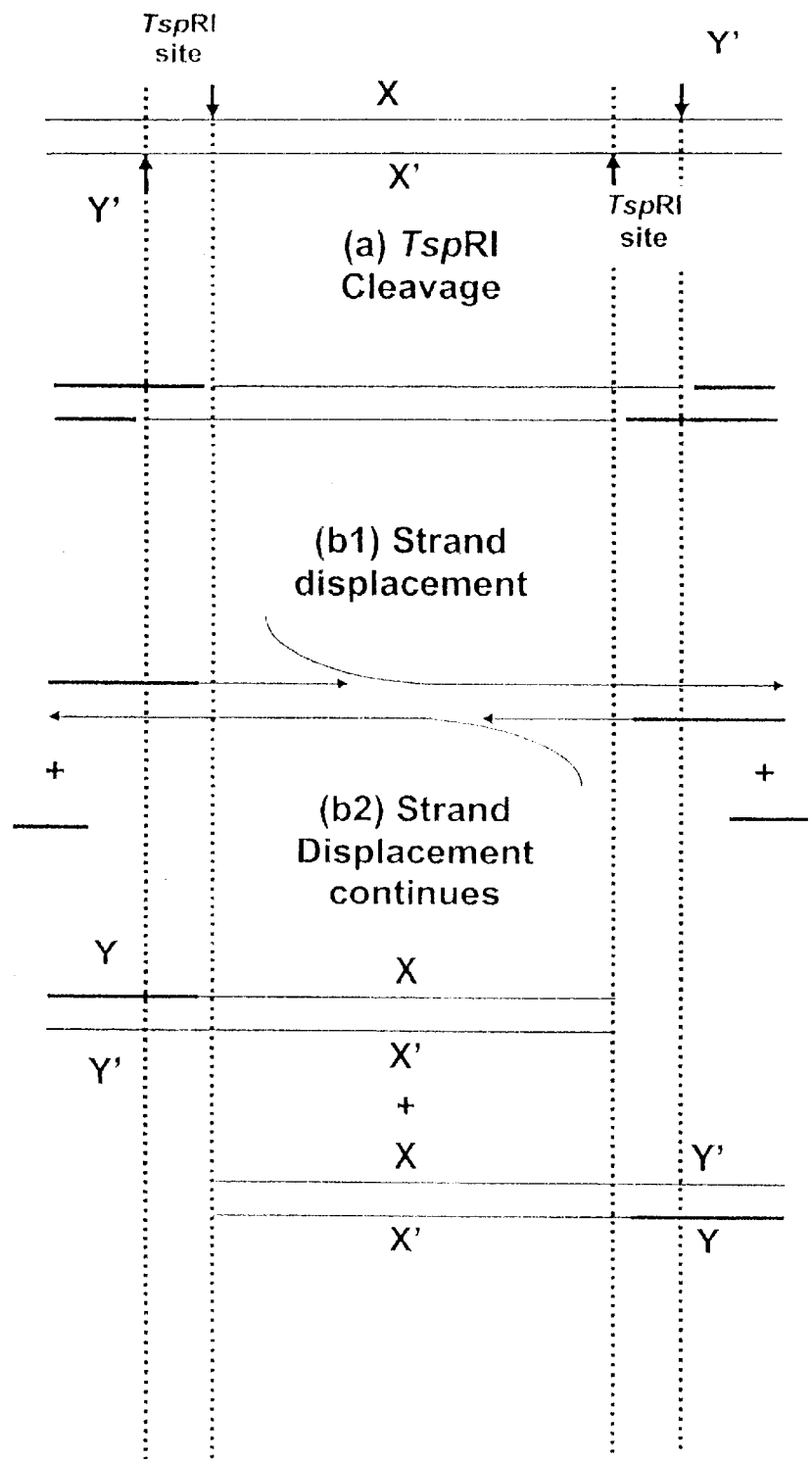
Figure 4B:
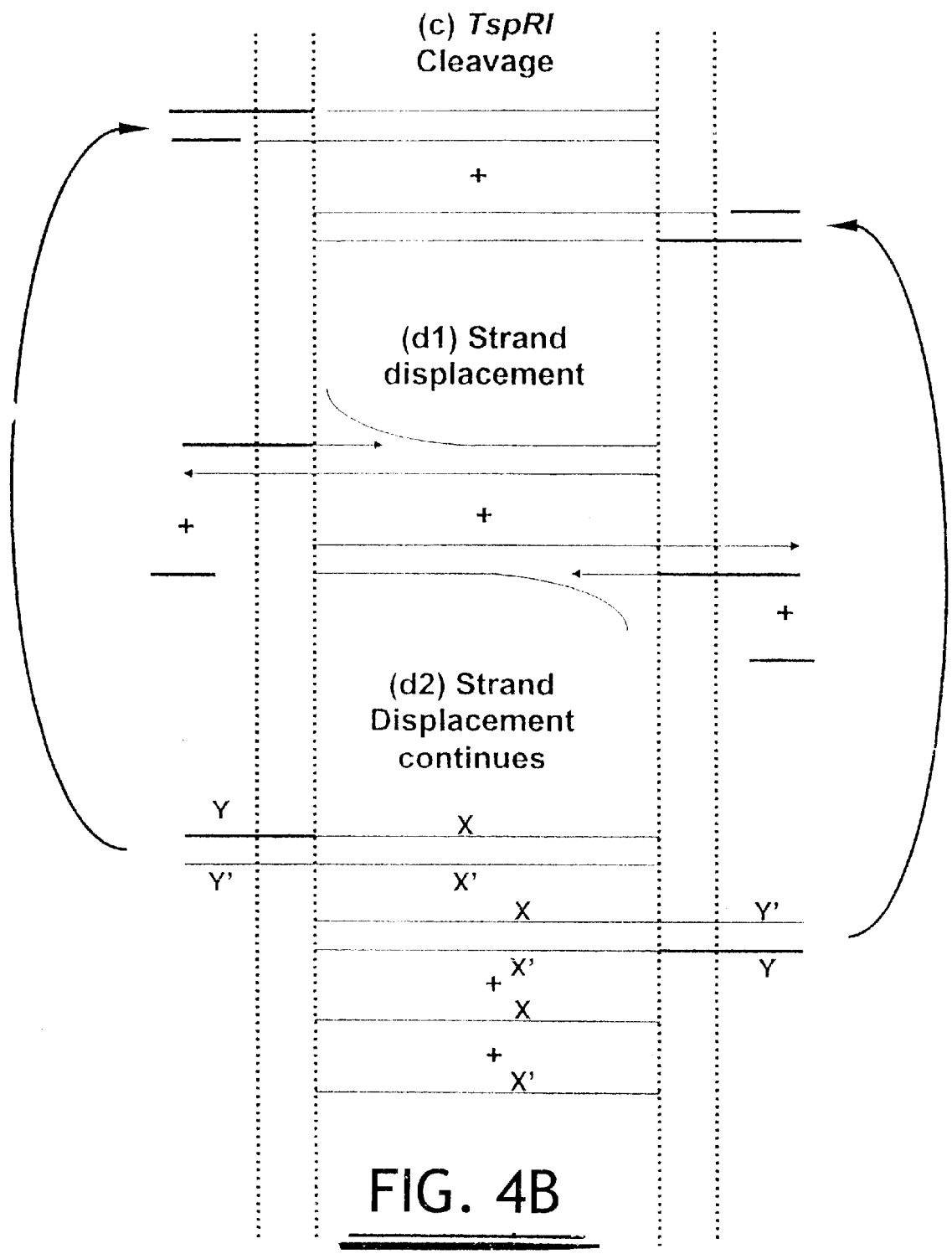
Figure 4C:
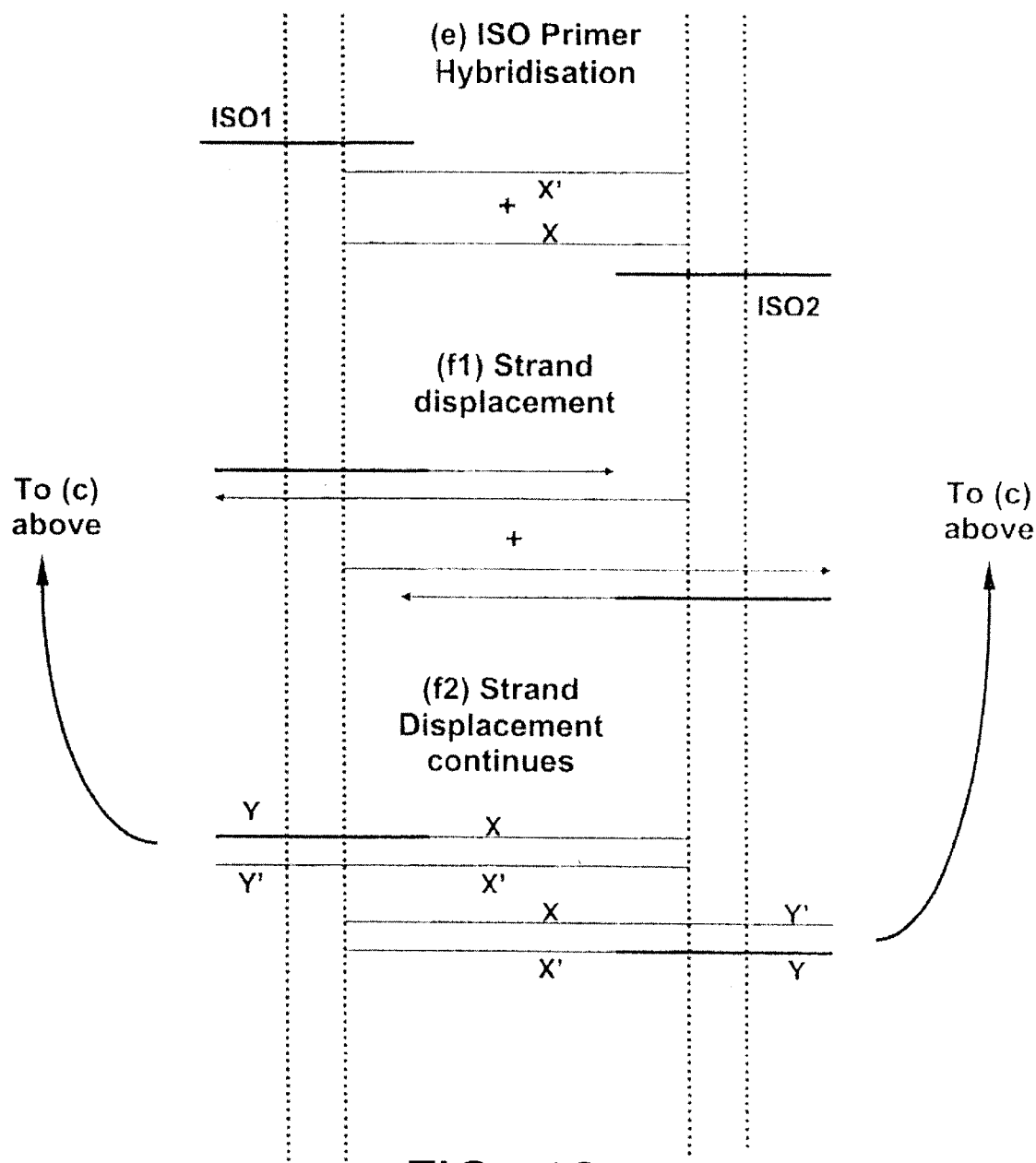

The invention will be further described by way of example only with reference to the accompanying drawings, in which FIG. 1 illustrates the recognition site for the restriction enzyme TspRI;

FIG. 2 schematically illustrates a DNA molecule for amplification in accordance with the method of the invention;

FIG. 3 schematically illustrates one embodiment of the method;

FIG. 4 schematically illustrates a further embodiment of the method;

FIGS. 5–11 illustrate the results of the Examples.

Referring to the drawings, FIG. 1 illustrates the restriction site of the enzyme TspRI. This recognition sequence comprises five base pairs as shown and the enzyme cuts two bases either side of the recognition sequence to produce a 9-base 3' overhang.

Reference is now made to FIG. 2 which illustrates a double stranded target DNA molecule 1 containing an internal sequence X (flanked by sequences Y and Y') to be amplified by the procedure described more fully below with reference to FIG. 3. With reference to these figures, the following convention will be used when referring to the composition of fragments. Sequences which are complementary are denoted by the same letters (or sequence of letters) but with one of the two complementary sequences additionally being denoted by the "prime" suffix ('). Thus X' is the complementary sequence to X.

When a molecule is composed of more than one segment it will be annotated from the 5' end of the molecule (thus the notation YXY' would be used to denote the upper strand of the molecule in FIG. 2). When a double stranded molecule is referred to the upper and lower sequences are separated by a slash (/) with both annotated from their 5' ends. Thus the entire molecule shown in FIG. 2 can be denoted YXY'/YX'Y'.

The molecule shown in FIG. 2 has a TspRI restriction site towards each end thereof flanking the sequence X/X' with each site being spaced from its respective end of the molecule by a short (8 bp) sequence to distance the restriction site away from the 5' end of the molecule. These 8 bp sequences, which are identical at each end of the molecule, have been included because certain restriction enzymes are unable to cleave near the ends of DNA. It has not been reported whether TspRI behaves in this fashion so that this sequence may or may not be necessary. Likewise, the optimum length of this sequence has not been reported and so this spacer may contain more or less than 8 bases.

It will be appreciated that the 17 base sequences at the 5' ends of the two strands (A and B) of the molecule 1 are identical and are referenced in FIG. 2 as Y and Y'.

In order to effect the amplification reaction, the molecule 1 is treated with the enzyme TspRI in the presence of a strand displacing polymerase, a primer FP1 having the aforementioned sequence Y, and the four nucleotides in a buffer such as conventionally used in amplification reactions.

A manner in which the reaction may proceed is illustrated in FIG. 3 in which the dashed vertical line is included purely to illustrate the relationship between the various steps of the process.

Initially, the molecule 1 is cleaved at both ends by TspRI so as to produce a "cleaved" molecule having 3' overhangs (each 9 bases) as illustrated as the result of step (a) in FIG. 3. In the next step, the primer FP1 (shown in bold for the purposes of clarity) hybridises to the "cleaved" molecule to produce the construct illustrated as the product of step (b) of FIG. 3. It should at this point be appreciated that exactly the same construct would be obtained if the short cleavage fragments of sequence Y nicked by the TspRI did not become denatured or if such denaturation did occur they became rehybridised.

In the next step, the strand displacing polymerase begins to extend each primer FP1 so that (with reference to the primer FP1 shown at the left hand end of FIG. 3) the primer FP1 is extended by copying strand X' as a template and simultaneously displaces the remainder of strand X. Similarly the other FP1 primer is extended by copying of strand X and displaces the remainder of strand X'. Simultaneously with extension of primers FP1, the 3' ends of the cleaved target molecule are extended using the FP1 primers as a template regenerating the restriction endonuclease sites. All of these copying reactions are schematically illustrated between steps (c1) and (c2) of FIG. 3.

For the purpose of simplicity, FIG. 3 shows the product of the strand displacement polymerisation (i.e. the product of step (c2)) to be two, foreshortened, double stranded copies of the original molecule (YX/X'Y' and XY'/YX'). It can be seen that each of these copies lacks one terminus of the original including the TspRI site at the end of the molecule.

As depicted, the next steps (steps (d) and (e)) involve cleavage of the molecules with TspRI and hybridisation of primers FP1 to the 3' overhangs produced. Once these primers are hybridised to the respective strands, strand displacing primer extension can occur as shown (steps (f1) and (f)). The products of this extension include two foreshortened double stranded molecules (YX/X'Y' and XY'/YX') essentially identical to the products of steps (c1) and (c2), These molecules are, therefore, available for further cycles of TspRI cleavage/hybridisation/extension (steps (d), (e) and (f1/f2)). The other products of step f ((f1) and (f2)) are two, further shortened, single strand sequences (X and X') which contain neither TspRI restriction site. These sequences are complementary, being copies of each strand of the central region of the original molecule.

With the method as thus far described, these single strands X and X' do not participate further in the amplification reaction. Amplification may however be greatly enhanced by incorporating, in the reaction mix, additional primers ISO1 and ISO2 (see FIG. 3(g)). ISO1 has a 5' terminal sequence corresponding to Y above whereas the remainder of the primer may be hybridised to the 3' end of sequence X' (FIG. 3(g)). Primer ISO2 also has 5' sequence corresponding to Y and the remainder of the primer may be hybridised to the 3' end of sequence X (FIG. 3 (g)) Polymerase extension, once again, "fills in" the molecules (steps (h1) and (h2)) to generate two foreshortened double stranded products. These molecules (YX/X'Y' and XY'/YX') are identical, in sequence terms, to the double stranded products of steps (c1/c2) and (f1/f2) described earlier, and so, are also able to re-enter further cycles of TspRI cleavage/hybridisation/extension (steps (d), (e) and (f1/f2)) described earlier.

Therefore, to summarise, each original molecule 1 undergoes a reaction resulting in the production of two shortened products lacking one or other terminal restriction site. Further processing of these molecules leads to their cyclical regeneration with the additional production of single stranded copies of each strand of the region between the TspRI sites in the original molecule. In the presence of the longer, target sequence specific ISO-primers (ISO1 and ISO2) these single strands are processed to generate further molecules identical to the earlier shortened double strands. The overall process is depicted in FIG. 3. The reaction thus cycles from (d) to (h) in a geometric manner.

It should be noted that primers ISO1 and ISO2 should be at much lower concentration than primer FP1 so that in step (b) of FIG. 3 there is a much higher probability of primer FP 1 hybridising to the 3'-overhang than either of ISO1 or ISO2 which could not then be extended to re-generate the restriction site.

For the purposes of simplicity, the description so far has assumed that the reaction occurs in "discrete" steps. Thus for example, with reference to steps (c1) and (c2) it has been assumed that the copying reactions illustrated therein are completed before any further cutting of the molecule. In practice, this may not actually be, the case since once the restriction site has been re-created it may be nicked once again before the copying reaction illustrated in steps (c1) and (c2) is completed This has not however effected the overall result of the process as described above.

A number of modifications may be made to the process.

For example, the process may be performed using two different sequences FP1 and FP2 instead of the single sequence FP1 as described.

Furthermore, under certain conditions, the cleavage site (generated by TspRI) may not dissociate prior to extension by nucleotide polymerase so that, under such conditions, the amplification reaction will proceed without the need to use primer FP1. This is illustrated in the procedure of FIG. 4 which, in many respects, is analogous to the procedure shown in FIG. 3, save that:

(i) the primers FP1 are not used and (ii) the cutting of double stranded molecules is shown to yield seventeen base pair fragments designated SF1, which do not dissociate from the molecule and which, as will be appreciated from FIG. 4, have a priming function in the same manner as primers FP1.

In further modifications of the procedure, alternatively or additionally there may be only one restriction site per molecule or different restriction sites at the opposite ends of the molecule.

Alternatively or additionally the restriction site may be that of a restriction enzyme other than TspRI.

It will be appreciated that, if the sequence to be amplified is present in a single stranded molecule then a double stranded molecule containing the required restriction site may be generated therefrom using known techniques.

The invention is illustrated by the following non-limiting Examples.

EXAMPLE 1

An amplification reaction was effected using the following templates, primers and reaction conditions.

Template 400 bp PCR fragment (Isofragment) generated from pUC19 using primers ISOS1 and ISOS2 below;

Primers: Two sequence-specific primers ISOS1 and ISOS2, and one Forcing Primer, ISOFP1 (equivalent to FP1 in FIG. 3) as shown below;

ISOS1 (SEQ ID NO. 1); 5'-TAATC TTTGG CAGTG GCTTA CAACG TCGTG ACTGG GAAAA C

ISOS2 (SEQ ID NO. 2): 5'-TAATC TTTGG CAGTG GCTGA CGGTG AAAAC CTCTG ACAC T

ISOFP1 (SEQ ID NO. 3): 5'-TAATC TTTGG CAGTG GC

Reaction Conditions:

20 $\mu$L New England Biolabs Buffer 4

10 $\mu$L Isofragment (50 fmol $\mu L^{-1}$)

5 $\mu$ dNTPs (10 nM each)

1 $\mu$L ISOS2 (4 pmol $\mu L^{-1}$)

2 $\mu$L ISOS1 (2.2 pmol $\mu L^{-1}$)

1 $\mu$L ISOFP1 (40 pmol $\mu L^{-1}$)

5 $\mu$TspR1 (5 U $\mu L^{-1}$)

1$\mu$L Bovine Serum Albumen (NEB 100× concentrated)

170 $\mu$L H$_2$O

A mix containing the three primers (ISOS1 and ISOS2 at approx. 20 fmol $\mu L^{-1}$, and ISOFP1 at approx. 200 fmol $\mu L^{-1}$), deoxyribonucleotides (250 $\mu$molL$^{-1}$ each), and template (Isofragment 2 at 2.5 fmol $\mu L^{-1}$) was equilibrated (in a water bath) to 65° C. when 25 U TspRI restriction enzyme was added. The optimum temperature for cleavage of Isofragment 2 by TspRI is 65° C. and incubation was continued for 20 minutes to allow restriction to occur (FIG. 3(a)). The mix was transferred to a second water bath at 37° C. A short equilibration period (30 s–1 m) was then included to allow hybridisation of primers to exposed ssDNA ends of the fragment (FIG. 3(b)). 10U of Klenow (exo-) DNA polymerase was added to extend the hybridisation products, which had accumulated, following restriction, The extension reaction was continued for 5 m at 37° C. (FIG. 3(c1/c2)). The mix was transferred to the 65° C. water bath to initiate a second restriction cleavage by TspRI (FIG. 3(d)). Following 20 minutes digestion and 30 s–1 min hybridisation (FIG. 3(e) and (g)) further Klenow enzyme (10U) was added and extension continued for 5 minutes (FIG. 3. (f1/2) and (h1/2)). Since TspRI can survive incubation at lower temperatures (e.g. 37° C.) the initial amount input was sufficient for the entire reaction. In contrast, Klenow (exo-) is destroyed by prolonged incubation at 65° C. and so additional enzyme was added to the mix following each incubation at the higher temperature. The cycle of incubation at 65° C., hybridisation, Klenow addition and extension at 37° C. constitute the "cycles" of amplification. Samples (20 µL) were removed at the end of the cycle as necessary. The reaction in the samples taken was terminated immediately by the addition of 4 µL of agarose gel loading dye and samples were held at 4° C. until all samples were collected. The samples were then analysed by agarose gel electrophoresis in 1% (w/v) agarose gel, containing 0.5 µg mL$^{-1}$ ethidium bromide, in 1×TBE buffer.

Figure 5:
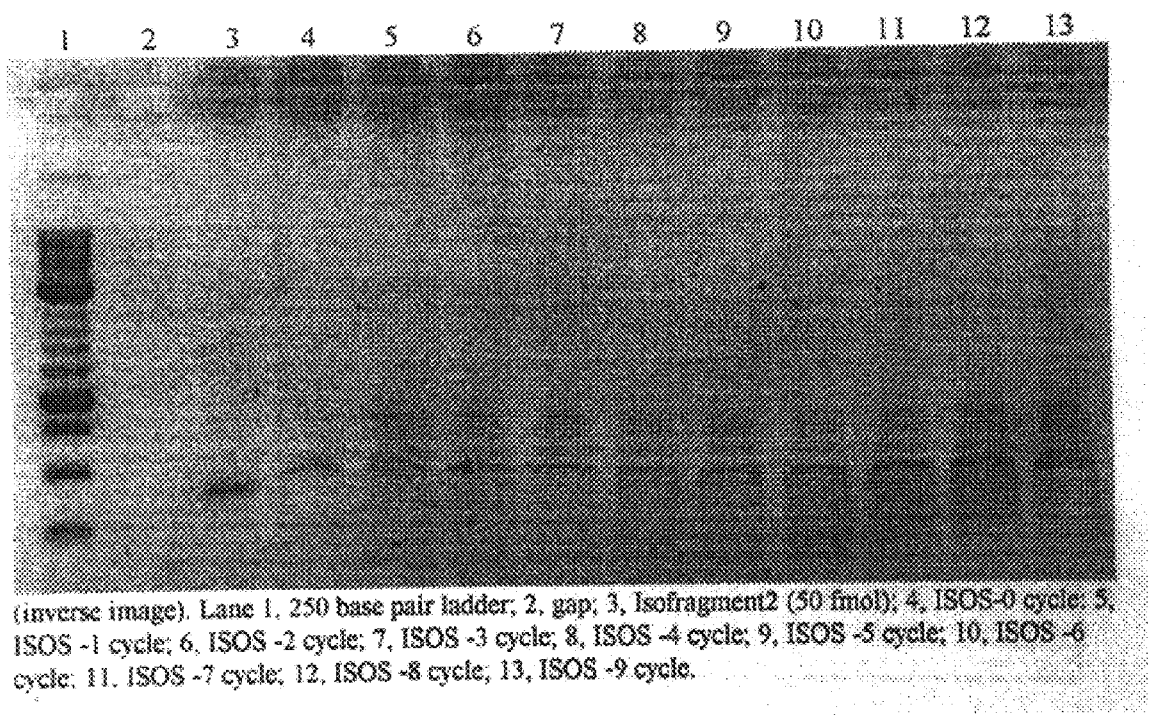

The results of this procedure are shown in FIG. 5 which demonstrates that amplification was clearly visible in all cases.

Figure 6:
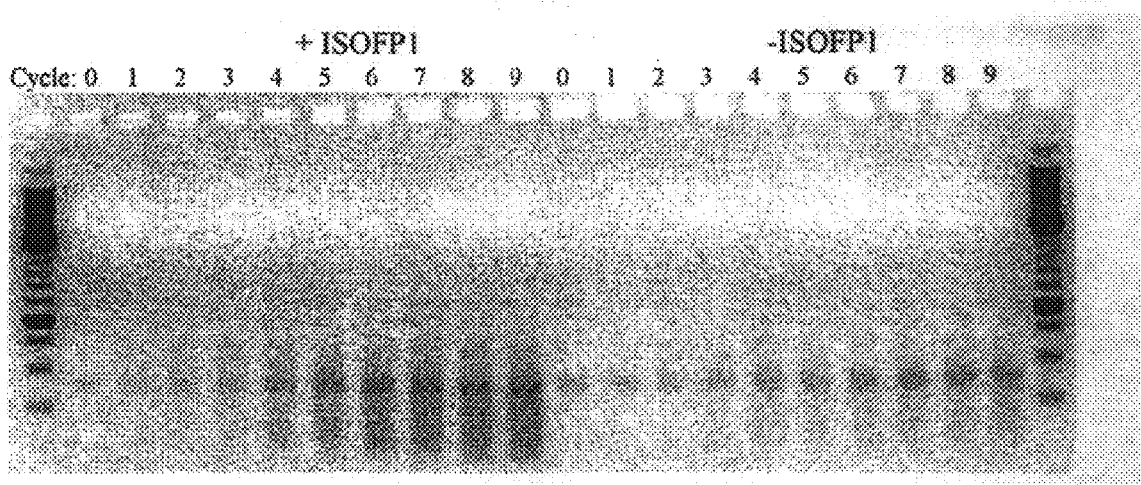

The above procedure was repeated but using an extension temperature of 39° C. instead of 37° C. A repeat was also conducted using the extension temperature of 39° C. but omitting the ISOFP1 primer from the reaction mix. The results of these procedures are shown in FIG. 6. The importance of including the primer ISOFP1 was clearly demonstrated by comparing amplification, at 39° C. in the presence and absence of the primer.

Figure 7:
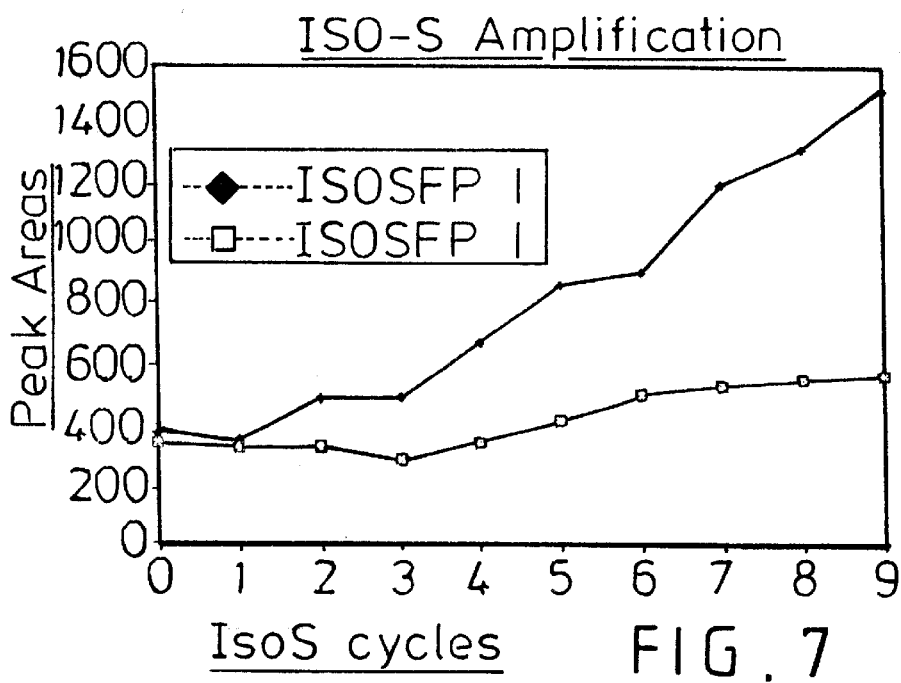

The effect of ISOFP1 on amplification can be quantified, to an extent, by using the gel scanning software (GELSCAN-UVP Ltd). To estimate peak heights or peak areas for the specific band being amplified (ca. 400 pairs). The results of peak area analysis for the gel photograph of FIG. 6 are illustrated in FIG. 7. These results show that there is considerable amplification of the fragment in the presence of ISOFP1. There is also a small, but significant, amplification in the absence of ISOFP1.

EXAMPLE 2

An amplification reaction was effected using the following template, primers and reaction conditions.
Template
Purified ISOCMV template (144 bp) at a concentration of 829 fmol/µl (produced by PCR of Cytomegalovirus using ISOCMV001 and ISOCMV002 primers).
CMV FRAGMENT (SEQ ID NO. 0.4)
5'-TTAAGTTACG CACTGAGGAA TGTCAGCTTC CCAGCCTCAA GATCTTCATC GCCGGGAACT CGGCCTACGA GTACGTGGAC TACCTCTTCA AACGCATGAT TGACCTAGC AGTATCTCCA CCGTCGAGAC AGTGGTGACA AGAC-3'
Primers
ISOCMV001 36-mer (SEQ ID NO. 5). 5' TTA AGT TAC GCA CTG AGG AAT GTC AGC TTC CCA GCC 3'
ISOCMV002 37-mer (SFQ ID NO. 6). 5' GTC TTG TCA CCA CTG TCT CGA CGG TGG AGA TAC TGC T 3'
FPCMV003 17-mer (SEQ ID NO. 7). 5' TTA AGT TAC GCA CTG AG 3'
FPCMV004 17-mer (SEQ ID NO. 8). 5' GTC TTG TCA CCA CTG TC 3'

FP primers were used at a concentration of 50 pmol/µl while the longer ISO primers were used at a concentration of 5 pmol/µl.
Reaction Conditions:

The following reactions were set up in 0.2 ml flat-topped thin-walled PCR tubes and incubated, following enzyme addition, at 65° C. (in a Biometra TRIO Thermoblock). The time points for incubation were 0, 20, 40 and 80 minutes. At the appropriate time, 61 µl of agarose gel loading dye was added to each reaction mix and samples were placed at 4° C. until all time points were completed.

| | |
|---|---|
| ISOCMV001 primer | 2 µl |
| ISOCMV002 primer | 2 µl |
| FPCMV003 primer | 2 µl |
| FPCMV004 primer | 2 µl |
| ISOCMV Template | 0.5 µl |
| 50 mM magnesium chloride (GIBCO) | 6 µl |
| 10 × Thermopolymerase buffer (New England Biolabs) | 3 µl |
| 10 mM dNTP (Pharmacia) | 1 µl |
| TspRI restriction enzyme, 5 U/µl (New England Biolabs) | 2 µl |
| Bst Polymerase, 4 U/µl (New England Biolabs) | 0.5 µl |
| 100 × Bovine Serum Albumin (New England Biolabs) (diluted to 1X with Molecular Biology grade water) | 9 µl |
| Total Reaction Volume | 30 µl |

Following incubation twenty microlitres of each sample was analysed by loading on a 10% polyacrylamide, 1×TBE (non-denaturing) gel using a Bio-Rad Mini-PROTEAN gel system. The gel was run for approximately 1 hour at 100–150V and then stained for 20–30 minutes in a solution of 0.5 mg/ml ethidium bromide/1×TBE (diluted from a stock of 10 mg/ml solution from Sigma).

The gel was visualised using a UV transilluminator and photographic system (MWG Biotech). An image of the gel is show in FIG. 8 and demonstrates considerable amplification under the conditions used.

EXAMPLE 3

Template: 400 bp PCR fragment (Isofragment) generated from pUC19 using primers ISOS1 and ISOS2 below;
Primers: Two sequence-specific primers ISOS1 and ISOS2, and one Forcing Primer, ISOFP1, as shown below;
ISOS1 (SEQ ID NO. 1):
5'-TAATCTTTGGCAGTGGCTTACAACGTCGTGACTG-GGAAAAC
ISOS2 (SEQ ID NO. 2):
5'-TAATCTTTGGCAGTGGCTGACGGTGAAAACCTCT-GACACAT
ISOIFP1 (SEQ ID NO. 3): 5'-TAATCTTTGGCAGTGGC
Reaction Conditions:
  20 µL New England Biolabs Buffer 4
  10 µL Isofragment (50 fmol µL$^{-1}$)
  5 µL dNTPs (10 mM each)
  1 µL ISOS2 (4 pmol µL$^{-1}$)
  2 µL ISOS1 (2.2 pmol µL$^{-1}$)
  1 µL ISOFP1 (40 pmol µL$^{-1}$)
  5 µL TspRI (5 U µL$^{-1}$)
  1 µL Bovine Serum Albumen (NEB 100× concentrated)
  170 µL H$_2$O A mix containing the three primers (ISOS1 and ISOS2 at approx. 20 fmol µL$^{-1}$, and ISOFP1 at approx. 200 fmol µL$^{-1}$), deoxynucleotides (250 pmol µL$^{-1}$ each), and template (Isofragment 2 at 2.5 fmol µL$^{-1}$) was equilibrated (in a water bath) to 65° C., when 25 U of TspRI restriction enzyme was added. Incubation was continued for 20 minutes when the mix was transferred to a second water bath at 34° C. After a short equilibration period (30 s–1 m) 10U of Klenow (exo-) DNA polymerase was added and extension continued for 5 m at 34° C. prior to returning the mix to the 65° C. water bath to initiate another 'cycle' of amplification. Samples (20 µL) were removed at the end of the cycle as necessary. The reaction in samples taken was terminated immediately by the addition of 4 µL of agarose loading dye and samples were held at 4° C. until all samples were collected. The samples were then analysed by agarose gel electrophoresis in 1% (w/v) agarose gel, containing 0.5 lg $\mu L^{-1}$ ethidium bromide, in 1×TBE buffer.

Figure 9:
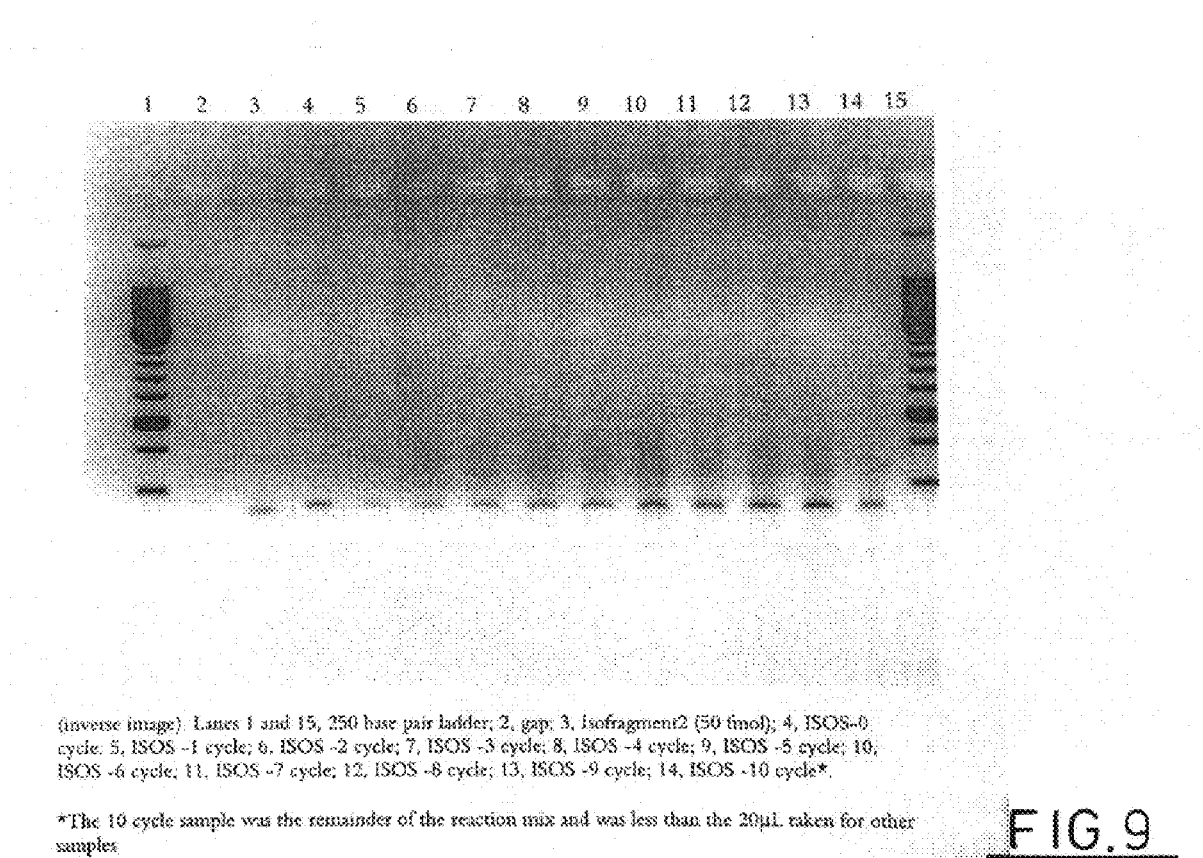

The results of this amplification procedure are shown in the gel photograph of FIG. 9 from which amplification is clearly demonstrated.

Figure 10:
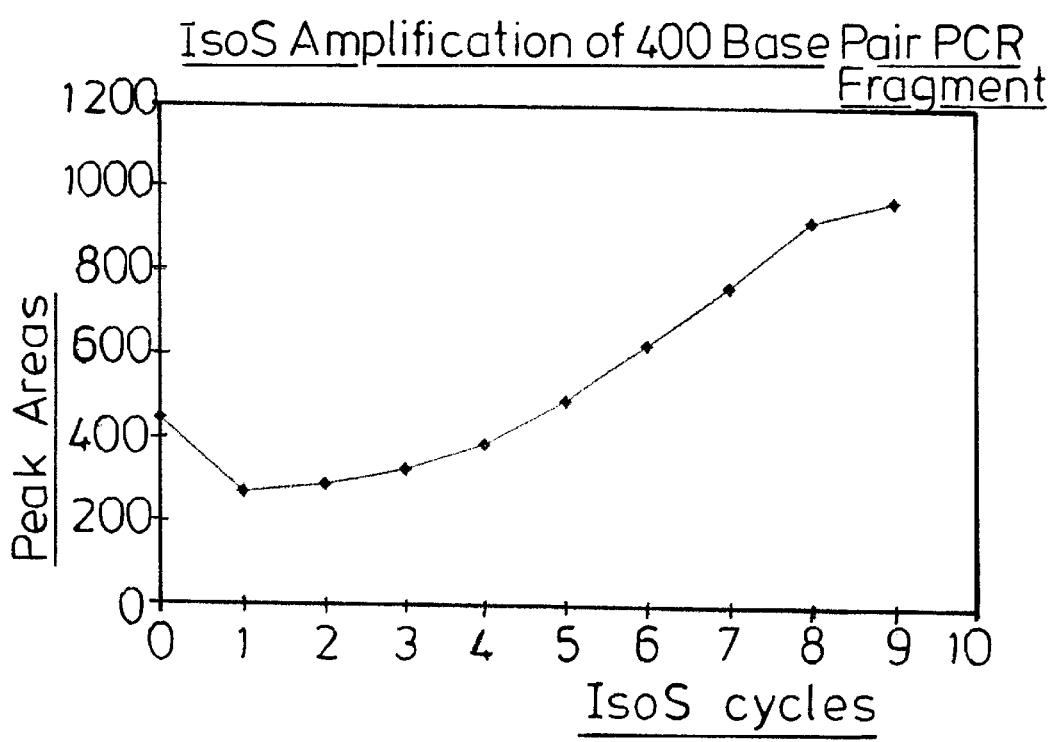
Figure 8:
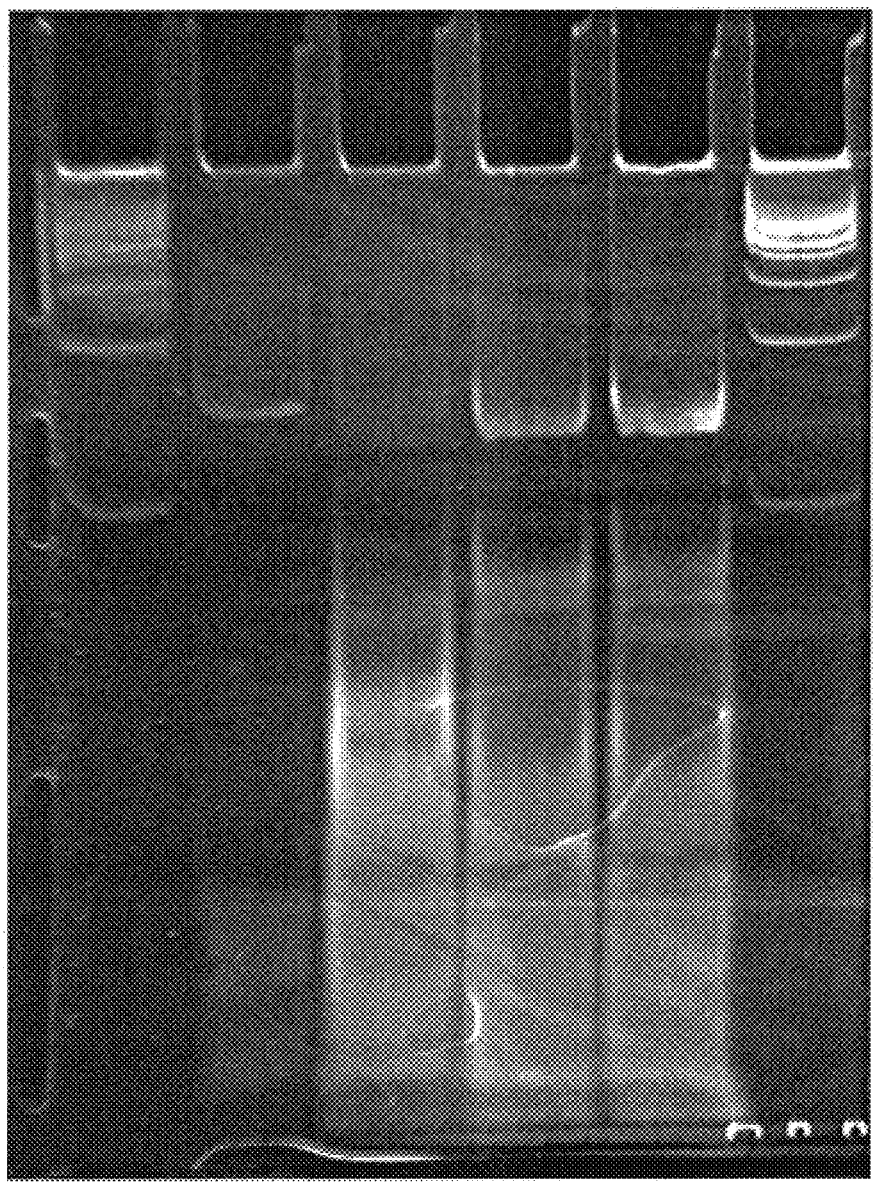

FIG. 10 is a plot showing the accumulation of product (400 bp band) based on peak area analysis of the GelBase/GelBlot analysis package (Ultra Violet Products Limited, Cambridge, UK). The 10 cycle value is not shown.

These results show that there was considerable amplification of the fragment.

EXAMPLE 4

Template: purified 144 bp PCR fragment (CMV144) generated from human cytomegalovirus DNA using ISOCMV001 and ISOCMV002-AT primers below (used at a final concentration of 760 fmol/$\mu$l).

Primers:
ISOCMV001 (36-mer) (SEQ ID NO. 5):
  5' TTA AGT TAC GCA CTG AGG AAT GTC AGC TTC CCA GCC 3'
ISOCMV002-AT (37-mer) (SEQ ID NO. 9):
  5' ATA TTG TAA CCA CTG TCT CGA CGG TGG AGA TAC TGC T 3'

Both primers were used at a concentration of 5 pmol/$\mu$l

Reagents:
  Wheat-germ tRNA @ 10 $\mu$g/ml (SIGMA) Lot 87H4045. Stock at 10 mg/ml
  50 mM magnesium acetate (SIGMA) Lot No. 77H10581
  10× Thermopolymerase buffer (New England Biolabs) Lot No. 20
  10 mM dNTP (Pharmacia, Polymerisation mix) Lot 7122094021
  TspRI restriction enzyme, 5U/$\mu$l (New England Biolabs) Lot No. 2
  Bst Polymerase, 8U/$\mu$l (New England Biolabs) Lot No. 13B
  Agarose Gel Loading dye, AGL007
  Molecular Biology grade water from ELGA water purifier Equipment:
  Biometra TRIO Thermoblock Method:
Template (CMV144) was diluted from the 760 fmol/$\mu$l stock using, serial tenfold dilutions. Concentrations of template used in the assay were 760 zmol/$\mu$l (456000 molecules/$\mu$l), 76 zmol/$\mu$l (45600 molecules/$\mu$l), 7.6 zmol/$\mu$l (4560 molecules/$\mu$l), 0.76 zmol/$\mu$l (456 molecules/$\mu$l), and 0.076 zmol/$\mu$l (456 molecules/$\mu$l).

The following reaction was set up in 0.2 ml flat-topped thin-walled PCR tubes, using each of the five template concentrations detailed above, and incubated at 56° C. for 2 hours.

| ISOCMV001 primer | 2 $\mu$l |
|---|---|
| ISOCMV002 primer | 2 $\mu$l |
| 50 mM MgAc | 5 $\mu$l |
| 10 mM dNTP | 0.5 $\mu$l |

| -continued | |
|---|---|
| 10 × Thermo buffer | 5 $\mu$l |
| TspRI | 1.5 $\mu$l |
| Bst Polymerase | 0.5 $\mu$l |
| template (CMV144) dilutions | 0.5 $\mu$l |
| MB water up to 25 $\mu$l | 7.5 $\mu$l |
| Total Reaction Volume | 25 $\mu$l |

Fifteen microliters of sample was analysed by loading on a 10% polyacrylamide, 1×TBE (non-denaturing) gel using a Bio-Rad Mini-PROTEAN gel system. The gel was run for approximately 45 mins at 175V and then stained for 10 minutes in a solution of 0.5 mg/ml ethidiumn bromide/1× TBE (diluted from a stock of 10 mg/ml solution from Sigma).

Figure 11:
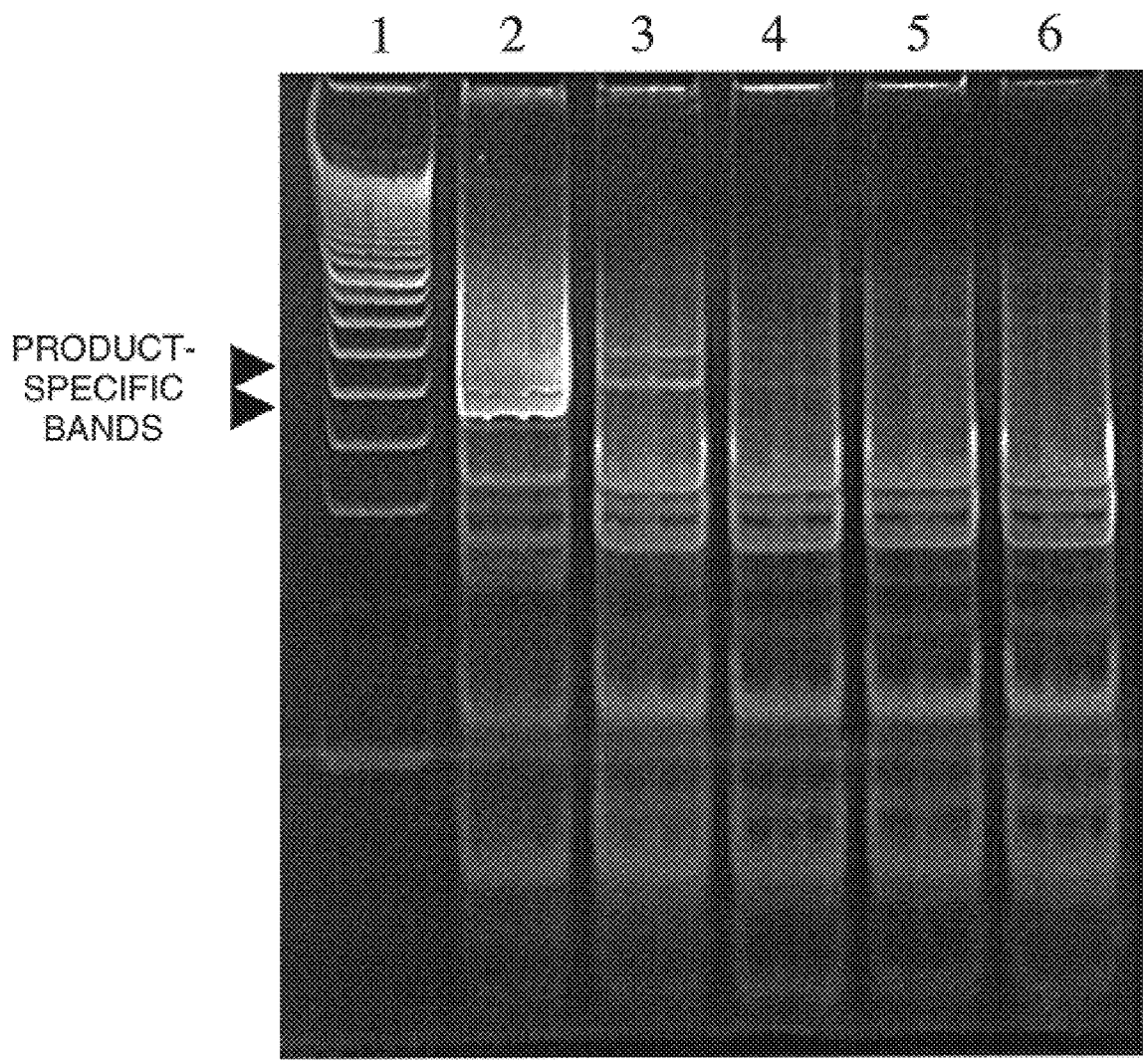

The gel was visualised using a UV transluminator and photographic system (MWG Biotech) The results of this amplification procedure are shown in the gel photograph of FIG. 11 from which amplification is clearly demonstrated.

In the above Examples, the targets used contained sites for the restriction enzyme, TspRI, which were introduced during their production. It will however be appreciated that suitable targets may be generated in a number of ways Such methods might include, but are not limited to:

1. Restriction digestion of long nucleic acid sequences carrying the target, to generate fragments with at least one known end. The restriction enzyme may, or may not, be that used for subsequent amplification, however, for exponential amplification the ISO primers must contain 3' sequences homologous to the 3' sequences of the fragment produced. Denaturation of the fragment (e.g. by elevated temperature) similar in structure to X and X' shown in FIG. 3. (F2) and thus the amplification would begin from that point.

2. Ligation of two synthetic oligonucleotides, using the target molecule as template, in a manner that such ligation generates a product which, when separated from the target by denaturation, as above, has a structure YX or YX' or YXY' or YX'Y', using the nomenclature as in FIG. 3. Such molecules would be a target for hybridisation by FP1 or an appropriate ISO primer, and would generate double stranded intermediates in the amplification cycle following polymerase extension.

3. Reverse transcription of an RNA target molecule with a primer containing the target specific sequence flanked by a sequence containing a suitably positioned restriction endonuclease site (ISO primer). Following separation of the RNA from the extended DNA copy product the addition of a target specific "downstreain" primer (or ISO primer) would initiate the amplification reaction.

What is claimed is:

1. A method of amplifying a nucleic acid sequence present in a first strand of a double stranded nucleic acid molecule comprised of complementary first and second strands wherein
said molecule incorporates an unmodified recognition site for a restriction enzyme capable of cutting the first strand at the 5' end of the sequence therein to be amplified and leaving the 3'-end region of the second strand projecting beyond the cut site in the first strand, and said method comprises
treating said nucleic acid molecule with said enzyme in the presence of a strand displacing polymerase and unmodified nucleotides for incorporation in an extending nucleic acid strand under conditions such that there is or becomes hybridised to said 3'-end region of the second strand a primer sequence complementary thereto whereby said primer sequence is extended in the 5' to 3' direction using the second strand as a template to re-generate the restriction endonuclease cut site and displace the sequence to be amplified.

2. A method as claimed in claim 1 wherein the nucleic acid molecule incorporates two of said restriction sites, one each side of the sequence to be amplified.

3. A method as claimed in claim 1 wherein the or each restriction site is a TspRI site.

4. A method as claimed in any one of claims 1 to 3 wherein the reaction mixture additionally incorporates an excess of oligonucleotide primers (FP) incorporating the restriction sequence and capable of hybridising to the 3' end of the displaced sequence whereby a double stranded molecule incorporating the restriction site is generated and the latter double stranded molecule is capable of participating in further cutting and extension/displacement reactions to generate strands which do not incorporate the restriction sequence.

5. A method as claimed in claim 1 wherein the reaction mixture additionally incorporates oligonucleotide primers (ISOS) incorporating the restriction sequence and being capable of hybridising to said strands which do not incorporate the restriction sequence.

6. A method as claimed in claim 1 wherein the nucleic acid is DNA.

7. A method as claimed in claim 1 wherein the strand displacing polymerase is 9° N. polymerase, Klenow (exo-) polymerase, Bst polymerase, Vent (exo-) polymerase, or Deep Vent (exo-) polymerase.

8. A method as claimed in claim 1 effected isothermally.

* * * * *

SEQUENCE LISTING

<160> NUMBER OF SEQ ID NOS: 9

<210> SEQ ID NO 1
<211> LENGTH: 41
<212> TYPE: DNA
<213> ORGANISM: Artificial Sequence
<220> FEATURE:
<223> OTHER INFORMATION: Sequence-specific primer

<400> SEQUENCE: 1
taatctttgg cagtggctta caacgtcgtg actgggaaaa c            41

<210> SEQ ID NO 2
<211> LENGTH: 40
<212> TYPE: DNA
<213> ORGANISM: Artificial Sequence
<220> FEATURE:
<223> OTHER INFORMATION: Sequence-specific primer

<400> SEQUENCE: 2
taatctttgg cagtggctga cggtgaaaac ctctgacact             40

<210> SEQ ID NO 3
<211> LENGTH: 17
<212> TYPE: DNA
<213> ORGANISM: Artificial Sequence
<220> FEATURE:
<223> OTHER INFORMATION: Forcing primer

<400> SEQUENCE: 3
taatctttgg cagtggc                                      17

<210> SEQ ID NO 4
<211> LENGTH: 144
<212> TYPE: DNA
<213> ORGANISM: Artificial Sequence
<220> FEATURE:
<223> OTHER INFORMATION: PCR product of Cytomegalovirus using
      ISOCMV001 and ISOCMV002 primers

<400> SEQUENCE: 4
ttaagttacg cactgaggaa tgtcagcttc ccagcctcaa gatcttcatc gccgggaact    60
cggcctacga gtacgtggac tacctcttca aacgcatgat tgacctcagc agtatctcca   120
ccgtcgagac agtggtgaca agac                                          144

<210> SEQ ID NO 5
<211> LENGTH: 36
<212> TYPE: DNA
<213> ORGANISM: Artificial Sequence
<220> FEATURE:
<223> OTHER INFORMATION: Sequence-specific primer

<400> SEQUENCE: 5
ttaagttacg cactgaggaa tgtcagcttc ccagcc                 36

<210> SEQ ID NO 6
<211> LENGTH: 37
<212> TYPE: DNA
<213> ORGANISM: Artificial Sequence
<220> FEATURE:
<223> OTHER INFORMATION: Sequence-specific primer

<400> SEQUENCE: 6

-continued

```
gtcttgtcac cactgtctcg acggtggaga tactgct                      37
```

<210> SEQ ID NO 7
<211> LENGTH: 17
<212> TYPE: DNA
<213> ORGANISM: Artificial Sequence
<220> FEATURE:
<223> OTHER INFORMATION: Forcing primer

<400> SEQUENCE: 7

```
ttaagttacg cactgag                                            17
```

<210> SEQ ID NO 8
<211> LENGTH: 17
<212> TYPE: DNA
<213> ORGANISM: Artificial Sequence
<220> FEATURE:
<223> OTHER INFORMATION: Forcing primer

<400> SEQUENCE: 8

```
gtcttgtcac cactgtc                                            17
```

<210> SEQ ID NO 9
<211> LENGTH: 37
<212> TYPE: DNA
<213> ORGANISM: Artificial Sequence
<220> FEATURE:
<223> OTHER INFORMATION: Sequence-specific primer

<400> SEQUENCE: 9

```
atattgtaac cactgtctcg acggtggaga tactgct                      37
```